United States Patent [19]
Thornton

[11] Patent Number: 5,718,244
[45] Date of Patent: Feb. 17, 1998

[54] EXTERNAL EAR OCCLUSION DEVICE HAVING AN IMPROVED DEFORMABLE MATERIAL AND METOD FOR FORMING SAME

[76] Inventor: W. Keith Thornton, 5524 Edlen, Dallas, Tex. 75220

[21] Appl. No.: 700,318

[22] Filed: Aug. 5, 1996

[51] Int. Cl.$^6$ ............................................. A61F 11/00
[52] U.S. Cl. .............................. 128/864; 128/887
[58] Field of Search ........................... 128/864–868, 128/887; 2/2

[56] References Cited

U.S. PATENT DOCUMENTS

| | | | |
|---|---|---|---|
| 3,897,376 | 7/1975 | Lampe | 128/864 |
| 4,459,247 | 7/1984 | Rothemund | 128/864 |
| 4,784,123 | 11/1988 | Robeson | 128/90 |
| 5,112,225 | 5/1992 | Diesso | 433/48 |
| 5,562,449 | 10/1996 | Jacobs | 433/37 |
| 5,573,015 | 11/1996 | Williams | 128/864 |

*Primary Examiner*—Michael A. Brown
*Attorney, Agent, or Firm*—Baker & Botts, L.L.P.

[57] ABSTRACT

An external ear occlusion device (10, 22) includes a deformable material (18) that conforms to the shape of at least a portion of a user's external ear to occlude the external ear. The deformable material (18) includes an aliphatic polyester, which may be a polycaprolactone polymer having the formula:

$$H[O(CH_2)_5C]_nO-R-O[C(CH_2)_5O]_nH$$

where R is an aliphatic hydrocarbon.

25 Claims, 1 Drawing Sheet

EXTERNAL EAR OCCLUSION DEVICE HAVING AN IMPROVED DEFORMABLE MATERIAL AND METOD FOR FORMING SAME

BACKGROUND OF THE INVENTION

In environments or during activities for which noise reduction is desirable, many persons use earplugs or other devices that occlude the ear canal to hinder the passage of sound, fluid, or other material to the eardrum. It is often desirable to improve the performance of such devices using a pliable material that conforms closely to shape of the external ear. Devices that do not properly conform to the shape of the outer ear may not adequately serve the purposes for which the devices are constructed.

As work environments, leisure activities, sleeping patterns, and other aspects of modern lifestyles become increasingly diverse, users or clinical professionals may wish to form an external ear occlusion device that more optimally fits the external ear to satisfy a variety of clinical, comfort, safety, durability, economic, and other requirements associated with particular users. A known technique for occluding the external ear includes inserting a deformable material into a user's ear canal to form an impression of the ear canal. The deformable material is cured, set, or otherwise hardened to form an earplug that hinders sound, fluid, or other materials from passing through the ear canal. The user inserts the earplug into the ear canal for a particular environment or activity, removes the earplug after modifying the environment or completing the activity, stores or disposes of the earplug, and inserts the same or a new earplug the next time the user encounters an environment or performs an activity for which ear canal occlusion is desirable. Such techniques may not be adequate for many users, however, because many of these earplugs may not conform to optimally fit particular users, resulting in external ear occlusion that is inadequate or dangerous for many applications. Moreover, the time, difficulty, and expense associated with the construction of these earplugs may make the cost prohibitive for many users.

SUMMARY OF THE INVENTION

In accordance with the present invention, the disadvantages and problems associated with external ear occlusion devices and methods having deformable materials have been substantially reduced or eliminated.

In accordance with one embodiment of the present invention, an external ear occlusion device includes a deformable material that conforms to the shape of at least a portion of a user's external ear to occlude the external ear. The deformable material includes an aliphatic polyester. In a more particular embodiment, the aliphatic polyester is a polycaprolactone polymer having the formula:

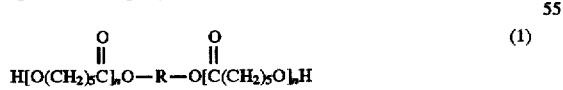

where R is an aliphatic hydrocarbon.

Important technical advantages of the present invention include providing an external ear occlusion device and method having an improved deformable material that more optimally conforms to and occludes the user's external ear. Improved external ear occlusion may be particularly important in certain environments or during certain activities in which the external ear is exposed to sound, fluid, or other materials that might impact, affect, apply pressure to, or damage the user's tympanic membrane or other sensitive structures of the external ear. The deformable material of the present invention displays desirable hardness, dimensional stability during cooling, biocompatibility, thermoplasticity, and bonding properties for a variety of contexts. Using this deformable material, the present invention provides an external ear occlusion device that is effective, efficient, comfortable, safe, reusable, and economical to serve the needs of particular users. Other technical advantages are readily apparent to one skilled in the art from the following figures, descriptions, and claims.

BRIEF DESCRIPTION OF THE DRAWINGS

For a more complete understanding of the present invention and for further features and advantages thereof, reference is now made to the following description taken in conjunction with the accompanying drawings, in which.

DETAILED DESCRIPTION OF THE INVENTION

Figure 1:
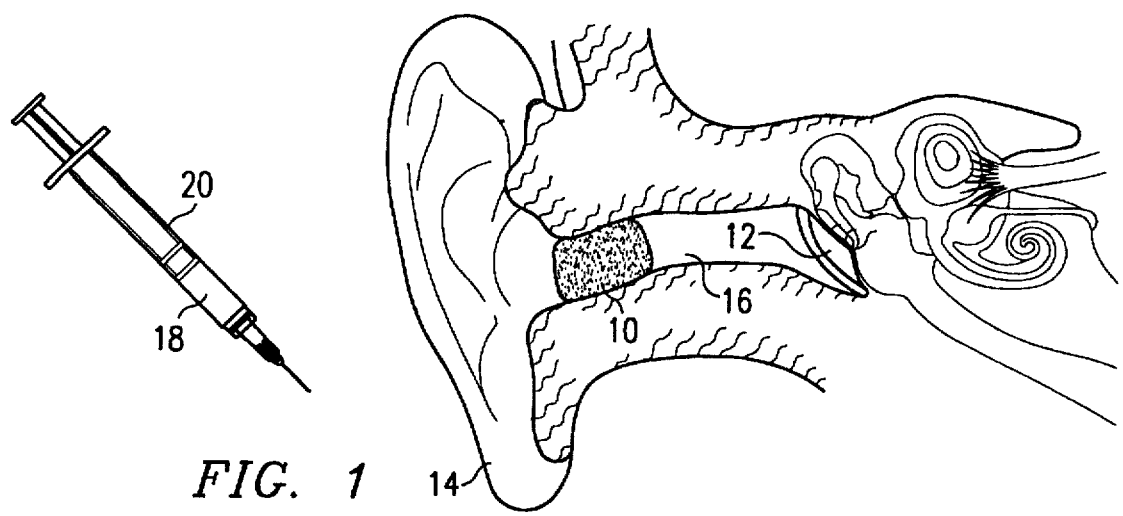
FIG. 1 illustrates an external ear occlusion device having an improved deformable material.

FIG. 1 illustrates an external ear occlusion device 10 positioned within a user's external ear to occlude the external ear. For purposes of this discussion, "external ear" refers generally to the outer, distal, or lateral portion of the user's ear, relative to the tympanic membrane 12, and includes, without limitation, the auricle 14, the ear canal 16, and other associated structures. When device 10 is positioned within the external ear, device 10 wholly or partially obstructs, restricts, plugs, blocks, or otherwise occludes the external ear to reduce or eliminate the passage of sound, fluid, or other materials through ear canal 16. As a result, device 10 hinders or prevents sound, fluid, or other materials to which device 10 is from reaching tympanic membrane 12 or other portions of the ear internal or medial to device 10.

Device 10 is formed using a deformable material 18 that includes one or more polycaprolactone polymers or other aliphatic polyesters described in U.S. Pat. Nos. 5,112,225 and 4,784,123, both of which are incorporated by reference herein, as well as in literature distributed by Union Carbide Corporation. Deformable material 18 may include any suitable polycaprolactone polymer or other aliphatic polyester, for example, and not by way of limitation, the TONE P-700, TONE P-767, and TONE P-787 polycaprolactone polymers manufactured by Union Carbide Corporation, taken singly or in any suitable combination. Polycaprolactone polymers may have the formula:

where R is an aliphatic hydrocarbon and n may range from approximately 300 to approximately 650. The present invention contemplates polycaprolactone polymers having other suitable formulas.

The TONE polycaprolactone polymers are described in U.S. Pat. Nos. 5,112,225 and 4,784,123, and in literature distributed by Union Carbide Corporation, as homopolymers, block copolymers, graft copolymers, or other polymers containing epsilon-caprolactone. Polymerization may be initiated using one or more diols, for example, and not by way of limitation, ethylene glycol, diethylene glycol, neopentyl glycol, butane diol, hexane diol, or any other suitable diol. One or more of these diols may have the formula:

HO—R—OH　　　　　　　　　　　　　　　(3)

where R is an aliphatic hydrocarbon.

In one embodiment, deformable material 20 includes approximately thirty (30) parts by volume TONE P-700 and sixty (60) parts by volume TONE P-767, together with approximately ten (10) parts by volume of one or more other polymers, depending on the application. A suitable light cured material, another polymer, or any other suitable material, such as a filler, coloring agent, stabilizer, antioxidant, or antimicrobial agent, may be used to replace or combine with one or more of the polycaprolactone polymers in forming deformable material 18 having any number of characteristics or properties, depending on the application for which device 10 is constructed.

Deformable material 18 may begin as one or more extruded pellets, beads, or rods of uniform, similar, or differing size, or in other suitable form. Deformable material 18 is heated in a microwave oven, in water or other non-solvent neutral liquid, or in any other suitable manner to between approximately 140 degrees Fahrenheit and approximately 180 degrees Fahrenheit to place deformable material 18 in its deformable state. Deformable material 18 may be kept in a deformable state until the pellets, beads, or rods congeal, coalesce, or otherwise combine to form a deformable mass capable of assuming a multitude of shapes and configurations.

In one embodiment, deformable material 18 is manually or automatically inserted into a suitable delivery device 20 before, during, or after deformable material 18 is placed in a deformable state. Delivery device 20 may include a syringe, hypodermic needle, hot glue gun, or other suitable source to deliver deformable material 18 to a selected region of the external ear. Deformable material 18 is delivered to and conforms to the shape of at least a portion of the external ear to wholly or partially occlude the external ear. The user or clinical professional may apply pressure to or otherwise influence deformable material 18 to properly conform deformable material 18. Deformable material 18 is then allowed to cool and harden or otherwise take a more permanent shape to form a mold of the external ear. These steps may be repeated as many times as necessary or desired to form a mold that conforms to the shape of at least a portion of the external ear using deformable material 18.

An important technical advantage of the present invention is that deformable material 18 cools more slowly and displays thermoplasticity at lower temperatures than materials such as the ethylene-vinyl acetate copolymer resin sold under the Registered Trademark ELVAX. This provides the user or clinical professional with more time to properly conform deformable material 18 to the external ear. In addition, deformable material 18 may display increased dimensional stability during the cooling process, relative to ELVAX, which may reduce or eliminate fitting problems and resulting inadequate external ear occlusion that might otherwise occur due to the tendency of materials such as ELVAX to contract during cooling.

Device 10 may remain inserted in the external ear or may be removed from the external ear before, during, or after deformable material 18 cools. Device 10 may be formed in a user's home, in the office of a clinical professional, or in any other suitable location. Device 10 may include a mold that conforms to the shape of one or more portions of the external ear, for example, the auricle, the ear canal, or both the auricle and ear canal, to occlude the external ear according to the particular user's needs. The present invention contemplates any suitable technique for forming a mold of at least a portion of the external ear using one or more polycaprolactone polymers or other aliphatic polyesters. When properly positioned, device 10 wholly or partially occludes the external ear to effectively, efficiently, comfortably, safely, and economically reduce or eliminate the passage of sound, fluid, or other materials.

Figure 2A:
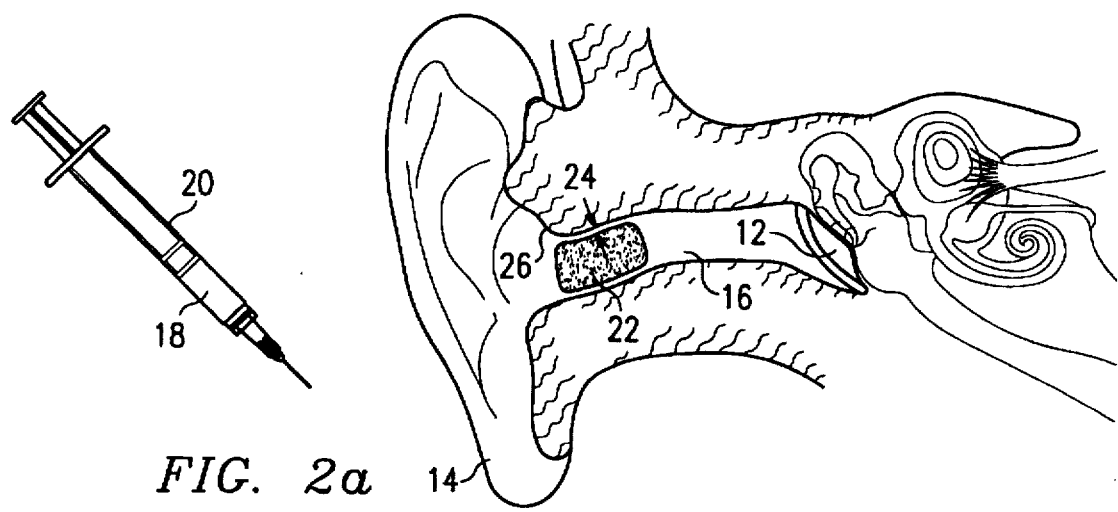
FIGS. 2a and 2b illustrate a method for relining an external ear occlusion device using an improved deformable material.
Figure 2B:
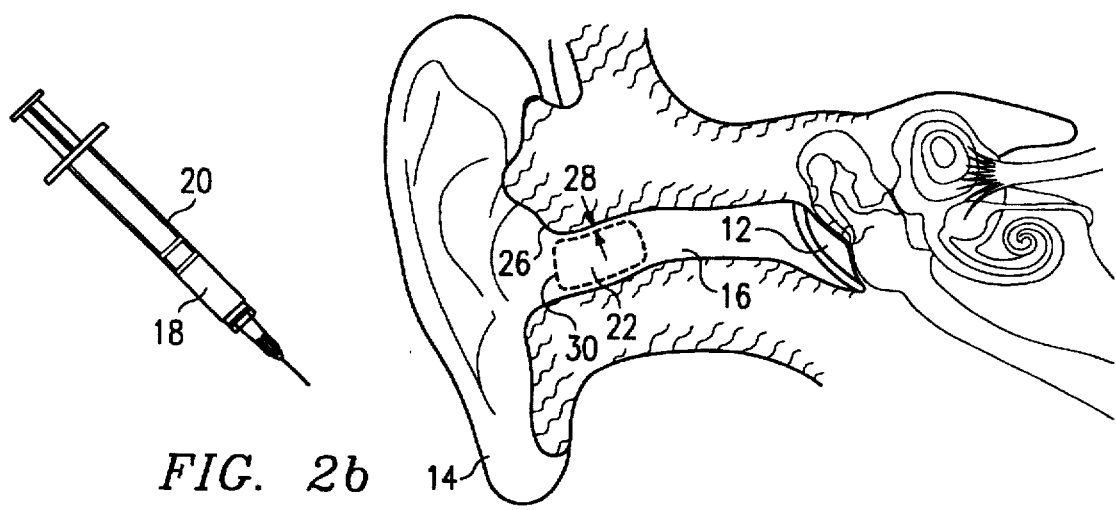

FIGS. 2a and 2b illustrate a method for relining an external ear occlusion device 22 using one or more of the polycaprolactone polymers or other aliphatic polyesters discussed above. A suitable light cured material, another polymer, or any other suitable material may be used to replace or combine with one or more of the polycaprolactone polymers in relining device 22. Referring to FIG. 2a, device 22 has been formed and inserted into a user's external ear to partially occlude the external ear. Due to improper formation or the tendency of deformable materials such as ELVAX to contract during cooling, however, device 22 does not optimally conform to the shape of the external ear. As a result, sound, fluid, or other materials may pass through the external ear to affect, impact, apply pressure to, or damage tympanic membrane 12. First offset 24 indicates the distance separating device 22 from the outward surface 26 of the external ear when device 22 is positioned within the external ear.

Deformable material 18 is introduced into the region between outward surface 26 and device 22 using delivery device 20, for example, a syringe, hypodermic needle, hot glue gun, or other suitable source. Deformable material 18 couples to device 22 and wholly or partially fills the region between device 22 and outward surface 26 of the external ear. As a result, first offset 24 is reduced or eliminated to yield a relined dental device 22 that more optimally conforms to the shape of the external ear to more fully occlude the external ear. Deformable material 18 may be delivered or introduced into the external ear and may couple to or otherwise combine with device 22 while deformable material 18 is in a liquid, melted, or other deformable state.

Deformable material 18 includes one or more of the polycaprolactone polymers or other aliphatic polyesters discussed above. Deformable material 18 may also include another polymer or any other suitable mixture, compound, composition, or material, depending on the application. As discussed above, deformable material 18 cools and hardens or otherwise takes a more permanent shape relatively slowly, and displays increased thermoplasticity during cooling, relative to materials such as ELVAX. This may provide the user or clinical professional with additional time to properly conform deformable material 18 to the shape of the external ear.

In one embodiment, although deformable material 18 wholly or partially surrounds and couples to device 22 while deformable material 18 is in a liquid or melted state, the user experiences little or no discomfort when deformable material 18 is introduced. This is due to a variety of factors, taken separately or in combination. First, since deformable material 18 includes one or more polycaprolactone polymers or other aliphatic polyesters, taken alone or together with one or more other suitable materials, deformable material 18 may transfer relatively little heat to the tissues of the external ear. Second, since deformable material 18 is introduced in a relatively thin layer, the volume of material that transfers heat to the tissues of the external ear is relatively small. As a result, the external ear is able to absorb the transferred heat with little or no discomfort. Other factors may also contribute to the user experiencing little or no discomfort when deformable material 18 is introduced into the external ear to reline device 22.

As shown in FIG. 2b, deformable material 18 couples to device 22 to form a relined device 22 that more optimally conforms to the shape of and more fully occludes the external ear. In one embodiment, deformable material 18 mixes, reacts, or otherwise combines with the material that originally formed device 22 to form relined device 22. A second offset 28 indicates the distance, if any, separating relined device 22 from outward surface 26 of the external ear. Although deformable material 18 may have a tendency to contract slightly as it cools, second offset 28 is smaller than first offset 24. As a result, relined device 22 more optimally conforms to the shape of the external ear than did original device 22 to more optimally occlude the external ear. This is due, at least in part, to the increased dimensional stability displayed by the polycaprolactone polymers or other aliphatic polyesters as deformable material 18 cools.

As indicated by the dashed lines 30, device 22 may remain inserted in or may be removed from the external ear before, during, or after deformable material 18 cools or otherwise hardens to form a mold of the external ear. Once device 10 has been formed or device 22 has been suitably relined according to the present invention, device 10 or device 22 may be repeatedly removed and reinserted as appropriate for the application for which device 10 and device 22 were constructed. Whether device 10 or device 22 is used, the external ear is more optimally occluded to shield and protect tympanic membrane 12 from sound, fluid, or other materials.

Although the present invention has been described above in connection with several embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. An external ear occlusion device, comprising:
   a deformable material operable to conform to the shape of at least a portion of a user's external ear to occlude the external ear, the deformable material comprising an aliphatic polyester.

2. The device of claim 1, wherein the aliphatic polyester comprises a polycaprolactone polymer.

3. The device of claim 1, wherein the aliphatic polyester has the formula:

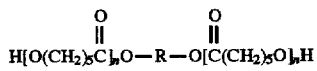

wherein R is an aliphatic hydrocarbon.

4. The device of claim 1, wherein the aliphatic polyester comprises a homopolymer of caprolactone initiated with a diol.

5. The device of claim 1, wherein the deformable material is dimensionally stable during cooling, relative to polyvinyl acetate.

6. The device of claim 1, wherein the deformable material further comprises a second polymer.

7. The device of claim 1, wherein the deformable material is operable to form a mold of at least a portion of the external ear.

8. The device of claim 1, wherein the deformable material conforms to the shape of the external ear while the deformable material is in a liquid state.

9. The device of claim 1, wherein the deformable material conforms to the shape of at least a portion of the user's ear canal.

10. A method for forming an external ear occlusion device, comprising:
    conforming a deformable material to the shape of at least a portion of a user's external ear, the deformable material comprising an aliphatic polyester, the deformable material operable to occlude the external ear.

11. The method of claim 10, wherein the aliphatic polyester comprises a polycaprolactone polymer.

12. The method of claim 10, wherein the aliphatic polyester has the formula:

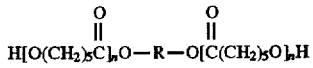

wherein R is an aliphatic hydrocarbon.

13. The method of claim 10, wherein the aliphatic polyester comprises a homopolymer of caprolactone initiated with a diol.

14. The method of claim 10, further comprising the step of combining a second polymer with the aliphatic polyester to form the deformable material.

15. The method of claim 10, further comprising the step of forming a mold of at least a portion of the external ear using the deformable material.

16. The method of claim 10, wherein the deformable material conforms to the shape of the external ear while the deformable material is in a liquid state.

17. The method of claim 10, wherein the deformable material is conformed to the shape of at least a portion of the user's ear canal.

18. The method of claim 10, further comprising:
    inserting an object into the external ear; and
    introducing the deformable material into the external ear to contact the object while the deformable material is in a liquid state.

19. A method for occluding a user's external ear, comprising:
    conforming a deformable material to the shape of at least a portion of the external ear, the deformable material comprising an aliphatic polyester, the deformable material operable to occlude the external ear.

20. The method of claim 19, wherein the aliphatic polyester comprises a polycaprolactone polymer.

21. The method of claim 19, wherein the aliphatic polyester has the formula:

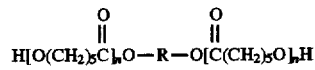

wherein R is an aliphatic hydrocarbon.

22. The method of claim 19, wherein the deformable material further comprises a second polymer.

23. The method of claim 19, further comprising:
    forming a mold of at least a portion of the external ear using the deformable material;
    removing the mold from the external ear; and
    inserting the mold into the external ear to occlude the external ear.

24. The method of claim 19, wherein the deformable material conforms to the shape of the external ear while the deformable material is in a liquid state.

25. The method of claim 19, wherein the deformable material is conformed to the shape of at least a portion of the user's ear canal.

* * * * *

UNITED STATES PATENT AND TRADEMARK OFFICE
CERTIFICATE OF CORRECTION

PATENT NO. : 5,718,244
DATED : Feb. 17, 1998
INVENTOR(S) : Thornton

It is certified that error appears in the above-identified patent and that said Letters Patent is hereby corrected as shown below:

Title page, [54], and col. 1, line 3, delete "METOD" and insert --METHOD--.

Signed and Sealed this

Twenty-first Day of April, 1998

Attest:

BRUCE LEHMAN

Attesting Officer

Commissioner of Patents and Trademarks